US00PP27223P3

(12) United States Plant Patent
Burton

(10) Patent No.: US PP27,223 P3
(45) Date of Patent: Oct. 4, 2016

(54) ***COPROSMA* PLANT NAMED 'SCARLETT 2'**

(50) Latin Name: *Coprosma repens*
Varietal Denomination: Scarlett 2

(71) Applicant: Stephen Burton, Cambridge (NZ)

(72) Inventor: Stephen Burton, Cambridge (NZ)

( * ) Notice: Subject to any disclaimer, the term of this patent is extended or adjusted under 35 U.S.C. 154(b) by 83 days.

(21) Appl. No.: 14/544,340

(22) Filed: Dec. 26, 2014

(65) Prior Publication Data

US 2016/0192556 P1 Jun. 30, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para

(57) ABSTRACT

A new cultivar of *Coprosma* plant named 'Scarlett 2' that is characterized by a compact habit, glossy leaves, young leaves that are grey-purple and mature leaves that are brown with grey-red margins.

1 Drawing Sheet

Botanical classification: *Coprosma repens.*
Variety denomination: 'Scarlett 2'.

BACKGROUND OF THE INVENTION

The present invention relates to a new and distinct cultivar of *Coprosma* plant botanically known as *Coprosma repens* and hereinafter referred to by the cultivar name 'Scarlett 2'.

The new cultivar was discovered by the inventor in a cultivated area of Cambridge, New Zealand in 2013. 'Scarlett 2' was discovered as a naturally occurring branch mutation of *Coprosma* 'Scarlett O'Hara' (not patented).

Asexual reproduction by tip cuttings of the new cultivar 'Scarlett 2' was first performed in 2013 in Cambridge, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Scarlett 2'.

1. *Coprosma* 'Scarlett 2' exhibits a compact habit.
2. *Coprosma* 'Scarlett 2' exhibits glossy leaves.
3. *Coprosma* 'Scarlett 2' exhibits young leaves that are grey-purple.
4. *Coprosma* 'Scarlett 2' exhibits mature leaves that are brown with grey-red margins.

The closest comparison cultivars are *Coprosma* 'Evening Glow' (not patented) and 'Tequila Sunrise' (U.S. Plant Pat. No. 18,392). The new cultivar 'Scarlett 2' is distinguishable from 'Evening Glow' by the following characteristics:

1. 'Scarlett 2' has mature leaves that are brown with grey-red margins. The mature leaves of 'Evening Glow' are green with yellow-green center blotches and red margins.

The new cultivar 'Scarlett 2' is distinguishable from 'Tequila Sunrise' by the following characteristics:

1. 'Scarlett 2' has mature leaves that are brown with grey-red margins. The mature leaves of 'Tequila Sunrise' are green with orange margins.

Plants of the new cultivar 'Scarlett 2' are distinguishable from the parent plant 'Scarlett O'Hara' by the following characteristics:

1. 'Scarlett 2' has longer lateral branches than the lateral branches of 'Scarlett O'Hara'.
2. 'Scarlett 2' has mature leaves that are brown with grey-red margins. The mature leaves of 'Scarlett O'Hara' are red-orange with light red margins.

BRIEF DESCRIPTION OF THE DRAWING

The accompanying photograph illustrates the distinguishing traits of *Coprosma* 'Scarlett 2'. The plant in the photograph shows an overall view of a 12 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Scarlett 2'. Data was collected in Cambridge, New Zealand from 12 month old outdoor grown plants in 2.5 liter containers. The time of year was Fall and the average temperature range was 18 to 22 degrees Centigrade during the day and 5 to 13 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Scarlett 2' has not been tested under all possible conditions and phenotypic differences may be observed with variations in environmental, climatic, and cultural conditions, however, without any variance in genotype.

Botanical classification: *Coprosma repens* 'Scarlett 2'.
Use: Ornamental perennial.
Parentage: 'Scarlett 2' is a naturally occurring branch mutation of *Coprosma* 'Scarlett O'Hara'.
Vigor: Moderate.
Growth rate: Moderate.

Growth habit: Freely branching, dense, bushy habit.
Plant shape: Broad upright inverted triangle.
Suitable container size: 2.5 liter container.
Height: Average 70-91 cm. in height.
Width: Average 70-91 cm. in width.
Low temperature tolerance: −2 degrees Centigrade.
High temperature tolerance: 38 degrees Centigrade.
Propagation: Tip cuttings.
Time to initiate roots: Approximately 40 days in the Summer at 20 degrees Centigrade and 45 days in the Winter at 18 degrees Centigrade.
Time to produce a rooted cutting: Approximately 120 days in the Summer at 20 degrees Centigrade and 200 days in the Winter at 18 degrees Centigrade.
Root system: Fine and fibrous.
Lateral branches:
*Quantity*.—Approximately 22.
*Dimensions*.—32 cm. in length and 3.5 mm. in diameter.
*Internode length*.—8 mm.
*Stem color*.—177A.
*Strength*.—Strong.
*Pinching*.—Yes, at 50 days.
Foliage:
*Texture*.—Smooth, glossy.
*Leaf arrangement*.—Opposite.
*Leaf attachment*.—Sessile.
*Compound or single*.—Single.
*Leaf shape*.—Obovate.
*Leaf apex*.—Obtuse.
*Leaf base*.—Rounded.
*Leaf length*.—Average 2.5 cm. in length.
*Leaf width*.—Average 1.5 cm. in width.
*Pubescence*.—Absent.
*Leaf margin*.—Entire, unevenly recurved, slightly wavy.
*Vein pattern*.—Pinnate.
*Young leaf color* (*upper surface*).—187A.
*Young leaf color* (*lower surface*).—187A.
*Mature leaf color* (*upper surface*).—N200A, margins 180A.
*Mature leaf color* (*lower surface*).—N200A, margins 180A.
*Durability of foliage to stress*.—Moderate to high.
Flowers: *Coprosma* 'Scarlett 2' has not produced flowers to date.
Disease and insect resistance: Plants of the new *Coprosma* have not been observed for disease or insect resistance.

The invention claimed is:

1. A new and distinct variety of *Coprosma* plant named 'Scarlett 2' as described and illustrated.

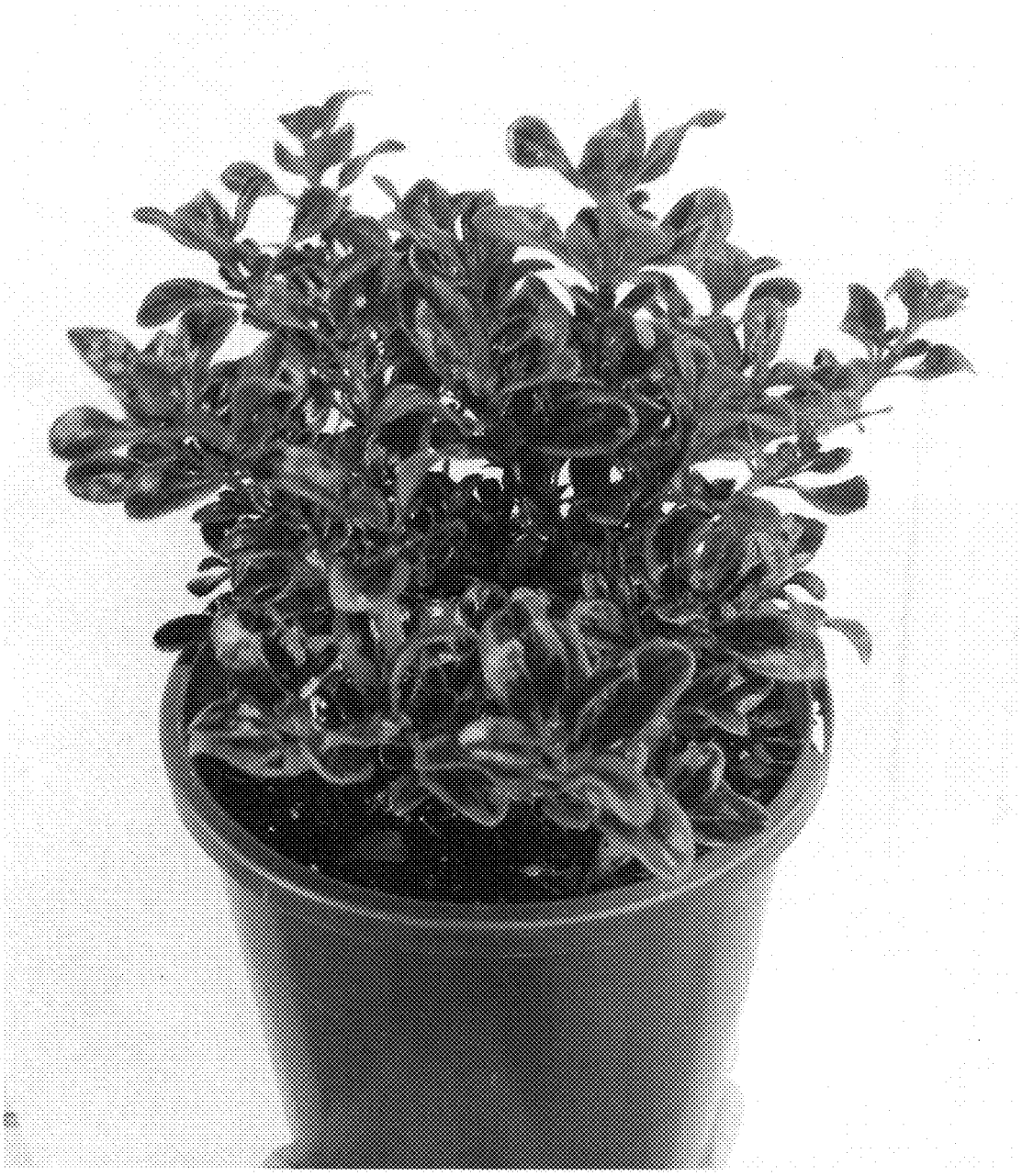

* * * * *